United States Patent
Gunn et al.

(10) Patent No.: US 7,528,100 B2
(45) Date of Patent: May 5, 2009

(54) DERIVATIZED POLYSACCHARIDE POLYMER

(75) Inventors: Euen Gunn, Trenton, NJ (US); Alvino Gabbianelli, Holland, PA (US); Regan Crooks, Hightstown, NJ (US); Krishnamurthy Shanmuganandamurthy, Plainsboro, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/282,501

(22) Filed: Nov. 18, 2005

(65) Prior Publication Data

US 2006/0111263 A1 May 25, 2006

Related U.S. Application Data

(60) Provisional application No. 60/629,402, filed on Nov. 19, 2004.

(51) Int. Cl.
*C11D 3/37* (2006.01)
*C11D 1/38* (2006.01)
*C11D 3/22* (2006.01)
*A61K 8/40* (2006.01)
*A61K 8/73* (2006.01)

(52) U.S. Cl. .......... 510/474; 510/119; 510/121; 510/123; 510/151; 510/155; 510/470; 424/401; 424/70.13; 424/70.19; 424/70.21; 424/70.22

(58) Field of Classification Search ........... 510/119, 510/121, 123, 151, 155, 470, 474; 424/401, 424/70.13, 70.19, 70.21, 70.22
See application file for complete search history.

(56) References Cited

U.S. PATENT DOCUMENTS

| | | | |
|---|---|---|---|
| 5,547,863 A | 8/1996 | Han et al. | 435/101 |
| 6,338,855 B1 | 1/2002 | Albacarys et al. | 424/409 |
| 6,627,184 B2 | 9/2003 | Coffindaffer et al. | 424/70.11 |
| 6,649,155 B1 | 11/2003 | Dunlop et al. | 424/70.27 |
| 2002/0082399 A1* | 6/2002 | Kuzee et al. | 536/17.4 |
| 2006/0029561 A1* | 2/2006 | Gunn et al. | 424/70.13 |

FOREIGN PATENT DOCUMENTS

FR 2795953 * 1/2001

* cited by examiner

*Primary Examiner*—Brian P Mruk

(57) ABSTRACT

Derivatized polysaccharide polymers that contain a fructan polymer substrate bearing one or more cationic substituent groups are useful in home and fabric care applications, in oilfield applications, and in emulsion polymerization applications.

20 Claims, No Drawings

DERIVATIZED POLYSACCHARIDE POLYMER

This application claims benefit of Provisional Application 60/629,402, filed Nov. 19, 2004.

FIELD OF THE INVENTION

This invention relates to polysaccharide polymers, more particularly, to derivatized polysaccharide polymers.

BACKGROUND OF THE INVENTION

Many shampoos and hair care products contain conditioning agents, which are typically high molecular weight polymers and which may be either synthetic or derived from natural sources. One benefit provided by conditioning agents is a reduction in the amount of work necessary to comb through the conditioned hair. Polymeric conditioning agents may also function as adjuvants in the delivery of supplemental conditioning agents, such as silicones.

There is a continuing interest in the art in developing hair conditioning agents that provide high conditioning performance at low concentrations.

SUMMARY OF THE INVENTION

In a first aspect, the present invention is directed to a derivatized polysaccharide polymer, comprising a fructan polymer substrate bearing one or more cationic substituent groups.

The derivatized polysaccharide polymer is useful as an ingredient in personal care compositions and may also be useful in home and fabric care applications, in oilfield applications, and in emulsion polymerization applications.

In a second aspect, the present invention is directed to a method for making a derivatized polysaccharide polymer, comprising;
(a) providing a fructan polymer substrate, said substrate comprising hydroxyl, hydroxalkyl, or hydroxyl and hydroxyalkyl substituent groups,
(b) adding cationic substituent groups to the polymer substrate by:
  (1) reacting at least a portion of the hydroxyl, hydroxalkyl, or hydroxyl and hydroxyalkyl groups of the fructan polymer substrate with a cationic compound, said cationic compound comprising a first functional group comprising a cationic moiety and a second functional group capable of reacting with such hydroxyl, hydroxalkyl, or hydroxyl and hydroxyalkyl groups, or
  (2) reacting at least a portion of the hydroxyl, hydroxalkyl, or hydroxyl and hydroxyalkyl groups of the fructan polymer substrate with a non-cationic nitrogenous compound, said non-cationic nitrogenous compound comprising a first functional group comprising a non-cationic nitrogenous moiety and a second functional group capable of reacting with such hydroxyl, hydroxalkyl, or hydroxyl and hydroxyalkyl groups to form non-cationic nitrogenous moieties on the fructan polymer substrate, and then rendering the nitrogenous moieties cationic, or
  (3) reacting at least a portion of the hydroxyl, hydroxalkyl, or hydroxyl and hydroxyalkyl groups of the fructan polymer substrate with a linking agent, said linking agent comprising a first functional group and a second functional group capable of reacting with such hydroxyl, hydroxalkyl, or hydroxyl and hydroxyalkyl groups to form reactive sites on the fructan polymer substrate and then
    (i) reacting the reactive sites with a cationic compound, said cationic compound comprising a first functional group comprising a cationic moiety and a second functional group capable of reacting with such reactive sites, or
    (ii) reacting the reactive sites with a non-cationic nitrogenous compound, said non-cationic nitrogenous compound comprising a first functional group comprising a non-cationic nitrogenous moiety and a second functional group capable of reacting with such reactive sites to form non-cationic nitrogenous sites on the fructan polymer substrate, and then rendering the nitrogenous sites cationic.

In a third aspect, the present invention is directed to a personal care composition, comprising a derivatized polysaccharide polymer comprising a fructan polymer substrate bearing one or more cationic substituent groups.

DETAILED DESCRIPTION OF INVENTION AND PREFERRED EMBODIMENTS

Fructan polymer substrates are polyfructose polymers of plant or microbial origin. The monomeric fructosyl units of the fructan polymer substrate may be linked by $\beta,2\text{-}1$, and/or $\beta,2\text{-}6$ linkages and the fructan polymer substrates typically exhibit some degree of branching. The monomeric fructosyl units are represented by formulae (I) and (II):

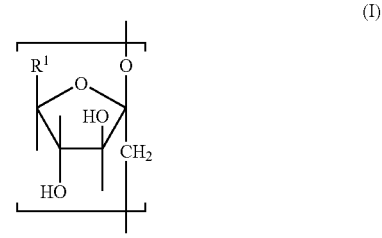

(I)

wherein:
each $R^1$ is independently $CH_2OH$ or $CH_2R^2$, and
$R^2$ is a fructosyl branch moiety comprising from 1 to 3 fructosyl monomeric units,

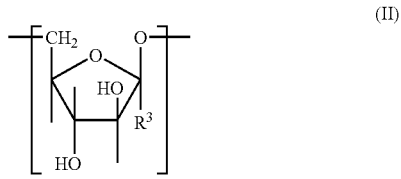

(II)

wherein:
each $R^3$ is independently $CH_2OH$ or $CH_2R^4$, and
$R^4$ is a fructosyl branch moiety comprising from 1 to 3 fructosyl monomeric units.

Typically, $R^2$ is a fructosyl branch moiety according to formula (III):

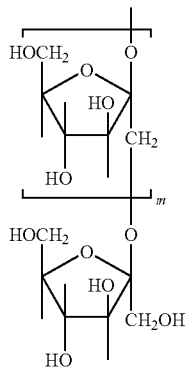

(III)

wherein m is 0, 1, or 2.

Typically, $R^4$ is a fructosyl branch moiety according to formula (IV):

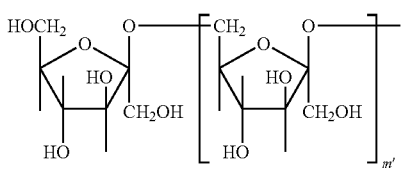

(IV)

wherein m' is 0, 1, or 2.

Fructans wherein the linkages between the fructosyl units of the polymer backbone are β,2-1 linkages are referred to as inulins and are represented by formula (V):

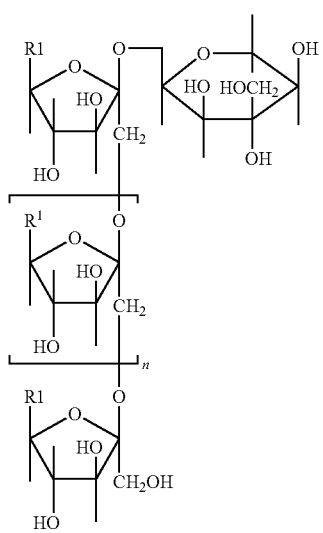

(V)

wherein $R^1$ is defined as above, and n is a number effective to provide a weight average molecular weight of from about $4 \times 10^3$ to about $1 \times 10^7$ Daltons, as measured by gel permeation chromatography.

Fructans wherein the linkages between the fructosyl units of the polymer backbone are β,2-6 linkages are referred to as levans and are represented by formula (VI):

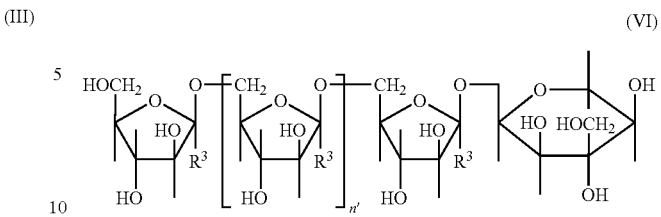

(VI)

wherein:

$R^3$ is defined as above, and n' is a number effective to provide a weight average molecular weight of from about $1 \times 10^4$ to about $1 \times 10^7$ Daltons, as measured by gel permeation chromatography.

Levans are produced by bacterial fermentation of sucrose substrates by a variety of microorganisms, including, for example, *Aerobacter aerogenes, Aerobacter levanicum, Xanthomonas pruni, Actinomyces viscosus*, and *Bacillus polymyxa*.

In one embodiment, levan exhibits a glass transition temperature of 138° C. and is available in particulate form.

The derivatized fructan polymer substrate is made by adding cationic substituents or non-cationic nitrogenous substituents to the polymer by reaction with at least a portion of the hydroxyl, hydroxalkyl, or hydroxyl and hydroxyalkyl groups of the polymer, either directly or via a linking agent, and in the case of the non-cationic nitrogenous substituents, rendering such substituents cationic.

Cationic substituents may be directly added to the fructan polymer substrate by reacting a cationic compound having a first functional group that comprises a cationic moiety, such as, for example a quaternary ammonium group, and a second functional group that is capable of reacting with the hydroxyl, hydroxyalkyl, or hydroxyl and hydroxyalkyl groups of the fructan polymer substrate by know synthesis methods, such as, for example, an epoxide, acid anhydride, acid halide, or ethylenically unsaturated group, to covalently bond the cationic moiety to the fructan polymer substrate. Suitable cationic compounds include cationic epoxide compounds, such as 2,3-epoxypropyltrimethylammonium chloride, and 2,3-epoxypropyldimethyl dodecylammoniumchloride.

Alternatively, non-cationic nitrogenous substituents may be added to the fructan polymer substrate by reacting a non-cationic nitrogenous compound having a first functional group that comprises a non-cationic nitrogenous moiety, such as, for example, a tertiary amino group, and a second functional group that is capable of reacting with the hydroxyl, hydroxyalkyl, or hydroxyl and hydroxyalkyl groups of the fructan polymer substrate by known synthesis methods, such as, for example, an epoxide, acid anhydride, acid halide, or ethylenically unsaturated group, to covalently bond the nitrogenous moiety to the fructan polymer substrate. Suitable nitrogenous compounds include, for example, dimethylaminopropyl methacrylamide.

Alternatively, cationic groups or non-cationic nitrogenous substituents may be added to the fructan polymer substrate via a two step process by reacting at least a portion of the hydroxyl, hydroxalkyl, or hydroxyl and hydroxyalkyl groups of the fructan polymer substrate with a linking agent, said linking agent comprising a first functional group and a second functional group capable of reacting with such hydroxyl, hydroxalkyl, or hydroxyl and hydroxyalkyl groups to form reactive sites on the fructan polymer substrate, and then reacting the reactive sites with a cationic compound having a first functional group comprising a cationic moiety and a second functional group comprising a moiety capable of reacting with such reactive sites, or with a non-cationic nitrogenous compound having a first functional group comprising a non-cationic nitrogenous moiety and a second functional group comprising a moiety capable of reacting with such reactive sites, in each case employing known synthesis techniques. In one embodiment, hydroxyl-functional poly(alkylene oxide) groups are bonded to the fructan polymer substrate by reacting one or more alkylene oxides, for example, ethylene oxide or propylene oxide, with at least a portion of the hydroxyl, hydroxyalkyl, or hydroxyl and hydroxyalkyl groups of the fructan polymer substrate and then an epoxy-functional cationic compound or non-cationic nitrogenous compound is reacted with the hydroxyl-functional poly(alkylene oxide) groups. In another embodiment, acid-functional groups are bonded to the fructan polymer substrate by reacting an a halo-functional organic acid, such as chloroacetic acid, with at least a portion of the hydroxyl groups of the fructan polymer substrate and then a hydroxyl-functional cationic compound or non-cationic nitrogenous compound is reacted with the acid-functional groups.

Non-cationic nitrogenous substituents may be rendered cationic by forming amine salts of all or a portion of the nitrogen atoms of such nitrogenous substituents, by quaternizing all or a portion of the nitrogen atoms of such nitrogenous substituents to form a quaternary ammonium salts, or by oxidizing all or a portion of the nitrogen atoms of such nitrogenous substituents to form N-oxide groups. For example, non-cationic nitrogenous moieties formed by reacting dimethylaminopropyl methacrylamide with hydroxyl, hydroxyalkyl, or hydroxyl and hydroxyalkyl groups of the fructan polymer substrate cationic are rendered cationic by reaction with 1-chloro-2-hydroxypropyl trimethyl ammonium chloride.

As used herein, the term "amine salt" in reference to a nitrogen atom of a nitrogenous polymer means a monomeric unit of the polymer containing the nitrogen atom, wherein such nitrogen atom is covalently bonded to from one to three organic groups and is associated with an anion. As used herein, the term "quaternary ammonium salt" in reference to a nitrogen atom of a nitrogenous polymer means a monomeric unit of the polymer, wherein such nitrogen atom is covalently bonded to four organic groups and is associated with an anion. As used herein, the term "quaternized" in reference to a compound means that the compound has at least one quaternary ammonium salt group per molecule.

In one embodiment, the derivatized polysaccharide polymer comprises one or more monomeric units selected from derivatized fructosyl units according to formula (VII):

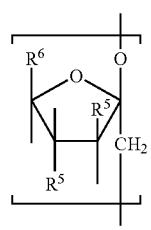

(VII)

and derivatized fructosyl units according to formula (VIII):

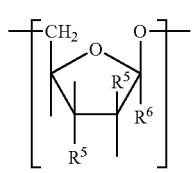

(VIII)

wherein:
wherein:
each $R^5$ is independently OH or $R^7$,
each $R^6$ is independently $CH_2OH$ or $CH_2R^7$, and
each $R^7$ is independently a cationic moiety.

In one embodiment, the derivatized polysaccharide polymer is a derivatized inulin polymer according to the formula (IX):

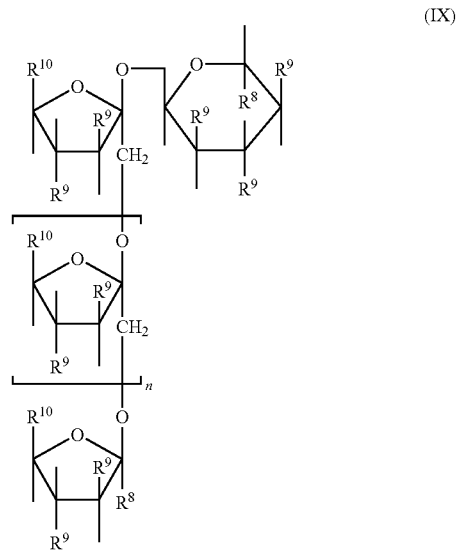

(IX)

wherein:
wherein:
n and $R^7$ are each as described above,
each $R^8$ is independently $CH_2OH$ or $CH_2R^7$,
each $R^9$ is independently OH or $R^7$,
each $R^{10}$ is independently $CH_2OH$, $CH_2R^7$, or $CH_2R^{11}$,
each $R^{11}$ is independently a fructosyl branch moiety according to structure (X):

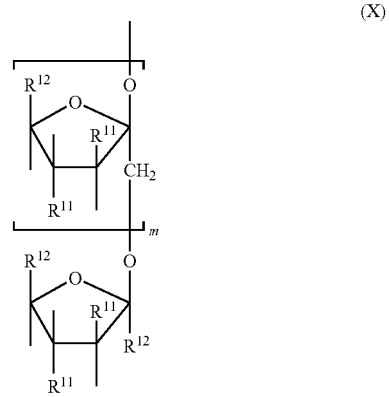

(X)

wherein:
each $R^{11}$ is independently OH or $R^7$,
each $R^{12}$ is independently $CH_2OH$ or $CH_2R^7$, and
m is as described above, provided that at least one $R^9$ is $R^7$, or at least one $R^{10}$ is $CH_2R^7$, or at least one $R^{10}$ is a fructosyl branch moiety according to formula (X) and at least one $R^{11}$ is $R^7$ or at least one $R^{12}$ is $CH_2R^7$.

In another embodiment, the derivatized polysaccharide polymer is a derivatized levan polymer according to the formula (XI):

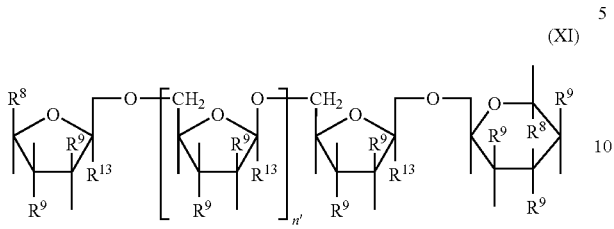

(XI)

wherein:
n', $R^7$, $R^8$, and $R^9$ are each as described above,
each $R^{13}$ is independently $CH_2OH$, $CH_2R^7$, or $CH_2R^{14}$,
each $R^{14}$ is independently a fructosyl branch moiety according to structure (XII):

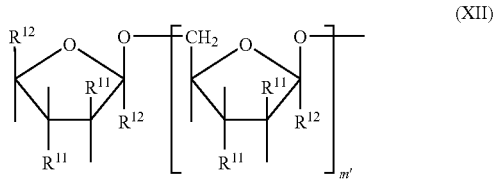

(XII)

wherein $R^{11}$, $R^{12}$ and m' are each as described above, provided that at least one $R^9$ is $R^7$, or at least one $R^{13}$ is $CH_2R^7$, or at least one $R^{13}$ is a fructosyl branch moiety according to formula (XII) and at least one $R^{11}$ is $R^7$ or at least one $R^{12}$ is $CH_2R^7$.

In one embodiment:
(a) a sufficient number of $R^9$ groups are $R^7$, and/or
(b) a sufficient number of $R^{10}$ or $R^{13}$ groups are $CH_2R^7$, and/or
(c) a sufficient number of $R^{10}$ or $R^{13}$ groups are fructosyl branch moieties according to formula (VIII) or formula (IX), and
(c)(i) a sufficient number of $R^{11}$ groups are $R^7$, and/or
(c)(ii) a sufficient number $R^{12}$ groups are $CH_2R^7$, that the cationic fructan polymer substrate exhibits a cationic charge density of greater than about 0.1 equivalents, more typically from about 0.5 to about 5 equivalents, and even more typically from about 1 to about 2 equivalents, per gram cationic fructan polymer substrate. As used herein, the "cationic charge density" of a polymer means the ratio of the average number of positive charges per molecule of the polymer to the weight average molecular weight of the polymer.

In one embodiment, $R^7$ comprises an amine salt moiety, a quaternary nitrogen salt moiety, or a nitrogen oxide moiety.

In one embodiment, $R^7$ is a group according to formula (XIII), (XIV), or (XV):

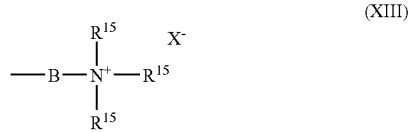

(XIII)

wherein:
B is a linking group,
each $R^{15}$ is independently $(C_1$-$C_{12})$alkyl, and
$X^-$ is an anion.

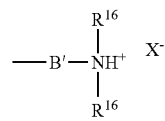

(XIV)

wherein:
B' is a linking group,
each $R^{16}$ is independently $(C_1$-$C_{12})$alkyl, and
X is an anion, and

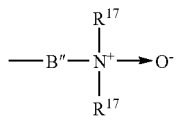

(XV)

wherein:
B" is a linking group,
each $R^{17}$ is independently $(C_1$-$C_{12})$alkyl, and
$X^-$ is an anion.

Suitable linking groups B, B', and B" include, for example, groups according to formulae (XVI) and (XVII):

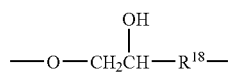

(XVI)

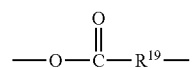

(XVII)

wherein each $R^{18}$ and $R^{19}$ is independently $(CH_2)_p$, and p is an integer of from 1 to 10.

In one embodiment, $R^7$ is a group according to formula (XVIII), (XIX), or (XX):

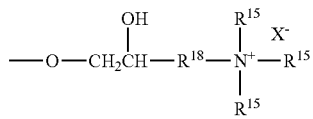

(XVIII)

wherein:
$R^{16}$, $R^{18}$ and $X^-$ are each defined as above,

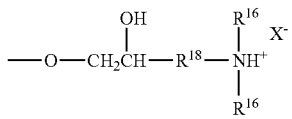

(XIX)

wherein $R^{16}$, $R^{18}$ and $X^-$ are each defined as above,

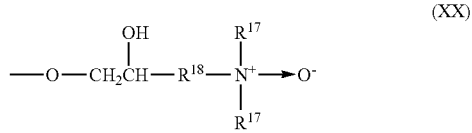

(XX)

wherein $R^{17}$ and $R^{18}$ are each defined as above.

It is believed that the cationic substituents of the cationic levan are bonded primarily to the outer surfaces of the levan particles and that the hydroxyl groups within the levan particle remain unreacted.

In one embodiment, mixtures of water and up to about 5 wt % cationic levan form clear solutions. Aqueous solutions of up to about 20 wt % cationic levan typically exhibit a viscosity of from about 10 centipoise to about 5000 centipoise. Aqueous solutions of greater than 20 wt % cationic levan typically exhibit a viscosity of greater than or equal to about 5000 centipoise.

Hair care compositions include, for example, cleansing compositions, such as body washes, shower gels, and shampoos, hair conditioners, and hair styling products, such as, for example, styling creams, gel, and mousses.

In one embodiment, the hair care composition of the present invention is an aqueous system. In one embodiment, the hair care composition comprises water and, based on 100 parts by weight (pbw) of the hair care composition, from about $1 \times 10^{-7}$ pbw to about 10 pbw, more typically from about 0.05 pbw to about 2.5 pbw, derivatized polysaccharide polymer.

In one embodiment, the hair care composition of the present invention contains one or more surfactant compounds. Surfactant compounds are characterized by the presence of both a hydrophilic group and a hydrophobic group on the same molecule and include amphoteric surfactants, Zwitterionic surfactants, nonionic surfactants, anionic surfactants, cationic surfactants or combinations thereof.

Anionic surfactants are ionic surfactant compounds that have a negative electrical charge associated with the hydrophilic portion of the surfactant. Any anionic surfactant that is acceptable for use in the intended end use application is suitable as the anionic surfactant component of the composition of the present invention. Examples of suitable anionic surfactants include, generally, alkyl sulfonates, aryl sulfonates, alkaryl sulfonates, alpha olefin sulfonates, paraffin sulfonates, alkyl ester sulfonates, alkyl sulfates, alkyl alkoxy sulfates, alkyl alkoxy carboxylates, alkyl alkoxylated sulfates, acylsarcosinates, and amidosulfonates, as well as mixtures thereof. Specific examples of suitable anionic surfactants include sodium tridecyl benzene sulfonate, sodium dodecyl benzene sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, ammonium cocyl sulfate, ammonium lauroyl sulfate, sodium cocyl sulfate, sodium lauroyl sulfate, potassium cocyl sulfate, potassium lauryl sulfate, monoethanolamine cocyl sulfate, sodium lauryl sarcosinate, sodium lauroyl sarcosinate, lauryl sarcosine, and cocyl sarcosine.

Cationic surfactants are ionic surfactant compounds that have a positive electrical charge associated with the hydrophilic portion of the surfactant. Any cationic surfactant that is acceptable for use in the intended end use application is suitable as cationic surfactant component of the composition of the present invention. Examples of suitable cationic surfactants are include compounds according to formula (XXI):

(XXI)

wherein:

each $R^{20}$ is independently hydrogen, an organic group, provided that at least one $R^{20}$ is not hydrogen.

X is an anion.

Suitable anions include, for example, chloride, bromide, methosulfate, ethosulfate, lactate, saccharinate, acetate or phosphate.

If one to three of the $R^{20}$ groups are hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine.

For quaternary ammonium compounds, each $R^{20}$ may independently be the same or different organic group, or alternatively, may be fused with another one $R^{20}$ groups to form, together with the nitrogen atom to which they are attached, a heterocyclic ring, but may not be hydrogen. Suitable organic groups include, for example, alkyl, alkoxy, hydroxyalkyl, and aryl, each of which may be further substituted with other organic groups. Suitable quaternary ammonium compounds include monoalkyl amine derivatives, dialkyl amine derivatives, and imidazoline derivatives.

Suitable monoalkyl amine derivatives include, for example, cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl-dimethyl-(2)hydroxyethyl ammonium dihydrogen phosphate (also known as hydroxyethyl cetyldimonium phosphate), bassuamidopropylkonium chloride, cocotrimonium chloride, distearyldimonium chloride, wheat germ-amidopropalkonium chloride, stearyl octyldimonium methosulfate, isostearaminopropal-konium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Suitable dialkyl amine derivatives include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bis-stearyldimonium chloride and mixtures thereof.

Suitable imidazoline derivatives include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Amphoteric surfactants are ionic surfactant compounds that are characterized by the presence of two ionic sites on the same molecule and which, depending on the pH of the surrounding medium, may carry a negative electrical charge, a positive electrical charge, or both a negative electrical charge and a positive electrical charge on the same molecule. Any amphoteric surfactant that is acceptable for use in the intended end use application is suitable as the optional amphoteric surfactant component of the composition of the present invention. Examples of suitable amphoteric surfactants include derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates, as well as alkyl iminopropionates, alkyl iminodipropionates and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

Zwitterionic surfactants are ionic surfactant compounds characterized by the presence of two ionic sites per molecule, wherein one of the ionic sites carries a positive electrical charge regardless of the pH of the surrounding medium and wherein the other ionic site may, depending on the pH of the surrounding medium, carry a positive charge. Any Zwitterionic surfactant that is acceptable for use in the intended end use application is suitable as the optional Zwitterionic surfactant component of the composition of the present invention. Examples of suitable Zwitterionic surfactants include those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, such as cocoamidopropyl betaine, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine and alkylamidopropylhydroxy sultaines.

Nonionic surfactants are surfactant compounds that do not dissociate into ions and that not have an electrical charge associated with them. Any nonionic surfactant that is acceptable for use in the intended end use application is suitable as the optional nonionic surfactant component of the composition of the present invention. Examples of suitable nonionic surfactants include compounds produced by the condensation of alkylene oxide groups (hydrophilic in nature) with an organic hydrophobic compound which may be aliphatic or alkyl aromatic in nature. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, alkanolamides surfactants, alkylpolyglycosides, and condensation products of aliphatic alcohols with from about 1 to about 25 moles of ethylene oxide. Specific examples of suitable nonionic surfactants include alkanolamides such as cocamide DEA, cocamide MEA, cocamide MIPA, PEG-5 cocamide MEA, lauramide DEA, and lauramide MEA; alkyl amine oxides such as lauramine oxide, cocamine oxide, cocamidopropylamine oxide, and lauramidopropylamine oxide; polysorbates and ethoxylated sorbitan esters such as sorbitan laurate, sorbitan distearate, PEG-80 sorbitan laurate, polysorbate-20, and polysorbate-80; fatty acids or fatty acid esters such as lauric acid, isostearic acid, and PEG-150 distearate; fatty alcohols or ethoxylated fatty alcohols such as lauryl alcohol, laureth-4, laureth-7, laureth-9, laureth-40, trideceth alcohol, C11-15 pareth-9, C12-13 Pareth-3, and C14-15 Pareth-11.

In one embodiment, the hair care composition of the present invention comprises, based on 100 pbw solids (that is absent water and other solvents) of such composition, up to about 6 pbw amphoteric surfactants, up to about 8 pbw Zwitterionic surfactants, up to about 20 pbw anionic surfactants, wherein the total amount of all surfactants ranges from about 6 pbw to about 25 pbw, more typically from about 10 pbw to about 20 pbw.

Hair care compositions according to the present invention may, optionally, further contain other ingredients, such as, for example, preservatives such as benzyl alcohol, methyl paraben, propyl paraben and imidazolidinyl urea, thickeners and viscosity modifiers such as block polymers of ethylene oxide and propylene oxide, electrolytes, such as sodium chloride, sodium sulfate, polyvinyl alcohol, and ethyl alcohol, pH adjusting agents such as citric acid, succinic acid, phosphoric acid, sodium hydroxide, sodium carbonate, perfumes, dyes, other conditioning agents such as organosilicon materials, including, silicone gums, polyorganosiloxane fluids, and silicone resins, that is, crosslinked polyorganosiloxane systems, active ingredients such as anti-dandruff agents (zinc pyrithion), vitamins or their derivatives such as Vitamin B, Vitamin E Acetate, and sequestering agents such as disodium ethylene diamine tetra-acetate.

In one embodiment, the hair care composition of the present invention comprises, based on 100 pbw of the hair care composition and independently for each such ingredient, up to about 10 pbw, preferably from 0.5 pbw to about 5.0 pbw, of such other ingredients, depending on the desired properties of the hair care composition.

In one embodiment, the personal care composition of the present invention is a skin or hair care composition comprising the derivatized fructan polymer and one or more active ingredients, typically water insoluble active ingredients, such as for example, fragrances, conditioning agents such as silicone oils, and anti-dandruff ingredients. It is believed that the derivatized fructan polymer of the present invention enhances deposition of such active ingredients on the hair. More typically, such skin or hair care composition further comprises an anionic surfactant. It is believed that the combined derivatized fructan polymer and the anionic surfactant are capable of forming coacervates, either in the composition or upon dilution of the composition, such as for example, during rinsing of the composition from the skin or hair, and that coacervate formation is a mechanism for enhancing deposition of the active ingredients on the skin or hair. As used herein, the term "coacervates" means a discontinuous phase comprising localized regions or droplets that comprise a higher relative amounts of derivatized fructan polymer and anionic surfactant than the overall composition. It is believed that such coacervates are capable of entrapping active ingredients and encouraging deposition of such active ingredients on the skin and hair.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol.106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid anti Interface Science, Vol. 140, No. 1, November 1990, pp 227-238.

Techniques for analysis of formation of complex coacervates are known in the art. For example, measurement of the comparative light transmittance of the composition, at any stage of dilution, can be used to identify formation of a coacervate phase, with a coacervate phase being identifiable on the basis of decreased light transmittance. Alternatively, microscopic analysis of the composition, at any chosen stage of dilution, can be used to identify formation of a coacervate phase, with a coacervate phase being identifiable as an additional emulsified phase in the composition. The use of dyes can aid in distinguishing the coacervate phase from other insoluble phases dispersed in the composition.'

In one embodiment, the composition comprises a discontinuous phase having higher relative amounts of derivatized fructan polymer and anionic surfactant than the overall composition.

In one embodiment, the composition does not comprises a discontinuous phase, but upon dilution of the composition with water, the dilute composition forms a discontinuous phase.

In one embodiment, the composition and the discontinuous phase each further comprise an active ingredient and the discontinuous phase aids in deposition of the active ingredient on the hair or skin.

In one embodiment, a hair care composition according to the present invention comprises, based on 100 pbw of the hair care composition, from about 0.01 pbw to about 5 pbw derivatized fructan polymer, more typically cationic levan, and from about 0.01 pbw to about 10 pbw of an organopolysiloxane fluid, such as for example, Mirasil™ DMCO dimethicone copolyol (Rhodia SA), and up to about 99.98 pbw water. In another embodiment, the hair care composition further comprises an anionic surfactant.

EXAMPLE 1

The dervatized polysaccharide polymer of Example 1 was made as follows. Levan polymer (Montana Biotech SE Inc.) was ground and screened through a 150 micron (μm) screen. A resin flask reactor equipped with a condenser, a stirrer, and a thermometer was charged with water (48 g). The screened levan (100 g, 0.614 moles)) was added to the flask and stirred until the levan dissolved in the water. A 25% aqueous solution of sodium hydroxide (12 g, 0.075 moles NaOH) was added to the flask over a period of 5 minutes. A 70% aqueous solution of 2,3-epoxypropyltrimethylammonium chloride (33.6 g, 0.156 moles QUAB® 151, Degussa) was added to the flask over 10 minutes. The flask and contents were heated in water bath to 60° C. and the reaction mixture was maintained at 60° C. for 90 minutes and then allowed to cool to room temperature. Once cooled, the reaction mixture was neutralized with acetic acid (7.4 g, as 50% solution) to give 175.5 of amber liquid product. 100 g of the product was washed 2 times with isopropyl alcohol ("IPA", $1^{st}$ wash, 930 g IPA, $2^{nd}$ wash 200 g IPA) to remove water by mixing the product with IPA for 10 minutes and then removing the supernatant liquid under vacuum to yield 80 g of slurry, which was then dried at 40-50° C. under vacuum until the moisture content was less than 1.0% to yield 58 g of dried product. The dried product was ground and screened through a 150 μm screen to yield a fine powder that was slightly yellow in color. A 1 percent by weight aqueous solution of the product exhibited a hazy appearance, a pH of 4.98, and a viscosity of less than about 10 centipoise. The percent nitrogen as determined by LECO nitrogen analyzer was 1.83%.

The hydrodynamic radii of the levan particles and of the derivatized levan of Example 1 were measured by light scattering for respective 0.1% aqueous solutions of levan and derivatized levan of Example 1. Greater than 70% by weight of the levan particles exhibited a hydrodynamic radius of about 56 nanometers ("nm") and greater than 70% by weight of the derivatized levan particles exhibited a hydrodynamic radius of about 76 nm.

EXAMPLES 2 AND 3 AND COMPARATIVE EXAMPLE C1

The composition of Example 2 was a 0.3 percent by weight (wt %) aqueous solution of the cationic levan of Example 1. The composition of Example 3 was an aqueous solution of the cationic levan of Example 1 (0.3 wt %) and Miracare BC-27 amphoteric surfactant blend (38.5 w %). The composition of Comparative Example C1 was water alone.

The hair conditioning performance of the compositions of Examples 2 and 3 and Comparative Example C1 was tested. Medium brown bleached hair tresses, each 2.0 gm in weight and measuring 2.54 cm wide by 16 cm long, were moistened with tap water, washed with 0.2 ml of the compositions of Example 2 or 3 or Comparative Example C1, and rinsed. The work required to comb of the wet tresses after rinsing was measured using a Dia-Stron miniature tensile tester. Six tresses were used for each treatment condition. Results are given in TABLE 1 below as mean values and the 95% Bonferroni interval for each set of measurements.

TABLE I

| Work (Joules) | Ex. 2 | Ex. 3 | C. Ex. C1 |
| --- | --- | --- | --- |
| Mean | 0.016 | 0.061 | 0.037 |
| 95% Bonferroni interval | −0.010 to 0.042 | 0.035 to 0.088 | 0.010 to 0.063 |

Previous combing studies indicate treatment with aqueous Miracare BC-27 base elicits a change in wet combing force of approximately 0.001 Joules. Consequently, the 0.061 Joule value obtained for the composition of Example 3 indicates improved conditioning compared to aqueous Miracare BC-27 alone.

EXAMPLE 4

The derivatized polysaccharide polymer of Example 4 was made as follows. Levan polymer (Montana Biotech SE Inc.) was ground and screened through a 150 micron (μm) screen. A resin flask reactor equipped with a condenser, a stirrer, and a thermometer was charged with water (48 g). The screened levan (100 g, 0.614 moles)) was added to the flask and stirred until the levan dissolved in the water. A 25% aqueous solution of sodium hydroxide (12 g, 0.075 moles NaOH) was added to the flask over a period of 5 minutes. A 70% aqueous solution of 2,3-epoxypropyltrimethylammonium chloride (17.06 g, 0.079 moles QUAB® 151, Degussa) was added to the flask over 10 minutes. The flask and contents were heated in water bath to 60° C. and the reaction mixture was maintained at 60° C. for 90 minutes and then allowed to cool to room temperature. Once cooled, the reaction mixture was neutralized with acetic acid (7.3 g, 50% solution). The product was washed 2 times with isopropyl alcohol ("IPA", $1^{st}$ wash, 500 g IPA, $2^{nd}$ wash 500 g IPA) to remove water by mixing the product with IPA for 10 minutes and then removing the supernatant liquid under vacuum which was then dried at 40-50° C. under vacuum. The dried product (Moisture=1.75%) was ground and screened through a 150 μm screen to yield a fine powder that was light brown in color. A 1 percent by weight aqueous solution of the product exhibited a hazy appearance, a pH of 6.6, and a viscosity of less than about 10 centipoise. The percent nitrogen as determined by LECO nitrogen analyzer was 1.12%.

EXAMPLE 5

The derivatized polysaccharide polymer of Example 5 was made as follows. Levan polymer (Montana Biotech SE Inc.) was ground and screened through a 150 micron (μm) screen. A resin flask reactor equipped with a condenser, a stirrer, and a thermometer was charged with water (48 g). The screened levan (100 g, 0.614 moles)) was added to the flask and stirred until the levan dissolved in the water. A 25% aqueous solution of sodium hydroxide (15.9 g, 0.099 moles NaOH) was added to the flask over a period of 5 minutes. A 70% aqueous solution of 2,3-epoxypropyltrimethylammonium chloride (134.7 g, 0.624 moles QUAB® 151, Degussa) was added to the flask over 5 minutes. The flask and contents were heated in water bath to 60° C. and the reaction mixture was maintained at 60° C. for 90 minutes and then allowed to cool to room temperature. Once cooled, the reaction mixture was neutralized with acetic acid (9.2 g, 50% solution). The product was washed 3 times with isopropyl alcohol ("IPA", $1^{st}$ wash, 500 g IPA, $2^{nd}$ wash 500 g IPA and $3^{rd}$ wash 500 g IPA) to remove water by mixing the product with IPA for 10 minutes and then removing the supernatant liquid under vacuum which was then dried at 40-50° C. under vacuum. The dried product (Moisture=1.64%) was ground and screened through a 150 μm screen to yield a fine powder that was light brown in color. A 1 percent by weight aqueous solution of the product exhibited a hazy appearance, a pH of 8.1, and a viscosity of less than about 10 centipoise. The percent nitrogen as determined by LECO nitrogen analyzer was 4.55%.

EXAMPLE 6

The conditioning shampoo formulation of Example 6 was made by mixing together, based on 100 pbw of such composition, 14 pbw sodium laureth-2 sulfate, 2 pbw cocoamidopropyl betaine, 1.6 pbw sodium chloride, and 0.3 pbw of the derivatized polysaccharide polymer of Example 1 above.

The series of dilute shampoo solution of Examples 6-1 to 6-4 were made as noted in TABLE II below (expressed in parts by volume ("pbv") by, in each case, adding a volume of the shampoo composition of Example 6 to a volume of water. The transmittance of each of the compositions of Example 6 and 6-1 to 6-4 were determined as follows. A magnetic stirrer and the probe for the Photometer 662 (Metrohm) were placed into the composition. The composition was agitated with the stirrer. The mixing was sufficiently gentle to avoid forming bubbles in the solution. After 5 minutes of agitation, the transmittance reading was taken.

TABLE II

| EX# | Volume Shampoo Composition (pbv) | Total Volume (pbv) | % Transmittance |
|---|---|---|---|
| 6 | 100 | 100 | 87 |
| 6-1 | 100 | 200 | 60 |
| 6-2 | 100 | 400 | 68.2 |
| 6-3 | 100 | 600 | 85 |
| 6-4 | 100 | 1000 | 98.8 |

The shampoo formulation of Example 6 was optically clear and exhibited a transmittance of 87%. The transmittance of the dilute shampoo solutions of the compositions of Examples 6-1 to 6-4 decreased as a function of dilution, indicating flocculation of the shampoo composition and coacervate formation upon dilution.

EXAMPLE 7 AND COMPARATIVE EXAMPLE C2

The conditioning shampoo composition of Example 7 is made by mixing 1 pbw poly(dimethyl siloxane) with 99 pbw of the shampoo formulation of Example 6. The composition of Comparative Example C2 is analogous to the composition of Example 7, but lacks the derivatized polysaccharide polymer component (that is, Comparative Example C2 contains 1 pbw of the silicone compound and 99 pbw of a composition shampoo comprising 14 pbw sodium laureth-2 sulfate, 2 pbw cocoamidopropyl betaine, and 1.6 pbw sodium chloride). The composition of Example 7 is used treat hair tresses. The treated tresses are dried. The tresses treated with the composition of Example 7 show greater deposition of poly(dimethyl siloxane) than the hair tresses treated with the composition of Comparative Example C2.

The invention claimed is:

1. A derivatized polysaccharide polymer, comprising a levan polyfructose polymer substrate bearing one or more cationic substituent groups, wherein the levan polyfructose polymer substrate comprises fructosyl units that are linked by β,2-6 linkages and comprises formula (XI):

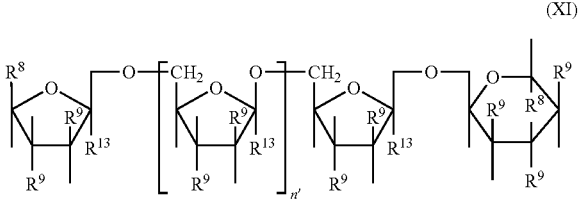

(XI)

wherein:
n' is a number effective to provide a weight average molecular weight of from about $1\times10^4$ to about $1\times10^7$ Daltons, as measured by gel permeation chromatography,
each $R^7$ is independently a cationic moiety
each $R^8$ is independently $CH_2OH$ or $CH_2R^7$,
each $R^9$ is independently OH or $R^7$,
each $R^{13}$ is independently $CH_2OH$, $CH_2R^7$, or $CH_2R^{14}$,
each $R^{14}$ is independently a fructosyl branch moiety according to structure (XII):

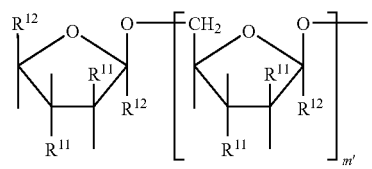

wherein
each $R^{11}$ is independently OH or $R^7$
each $R^{12}$ is independently $CH_2OH$ or $CH_2R^7$, and
each m' independently 0, 1, 2, or 3, and
provided that at least one $R^9$ is $R^7$, or at least one $R^{13}$ is $CH_2R^7$, or at least one $R^{13}$ is a fructosyl branch moiety according to formula (XII) and at least one $R^{11}$ is $R^7$ or at least one $R^{12}$ is $CH_2R^7$.

2. The polymer of claim 1, wherein each $R^7$ is independently selected from an amine salt moieties, quaternary nitrogen salt moieties, and nitrogen oxide moieties.

3. The polymer of claim 1, wherein $R^7$ is selected from groups according to formulae (XIII), (XIV), or (XV):

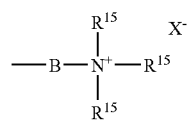

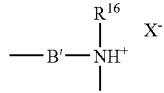

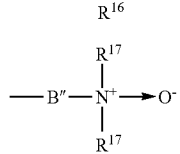

wherein:
each B, B', and B" is independently a linking group,
each $R^{15}$, $R^{16}$, and $R^{17}$ is independently $(C_1\text{-}C_{12})$alkyl, and
each X is independently an anion.

4. The polymer of claim 3, wherein B, B', and B" are each independently selected from groups according to formulae (XVI) and (XVII):

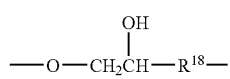

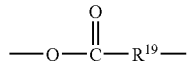

wherein each $R^{18}$ and $R^{19}$ is independently $(CH_2)_p$, and p is an integer of from 1 to 10.

5. The polymer of claim 1, wherein each $R^7$ is independently a group according to formula (XVIII), (XIX), or (XX):

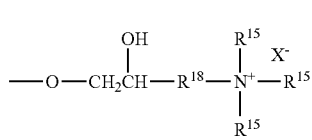

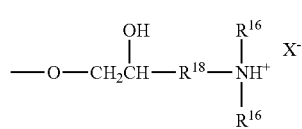

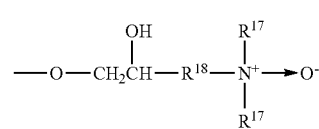

wherein
each $R^{15}$, $R^{16}$, and $R^{17}$ is independently $(C_1\text{-}C_{12})$alkyl,
each $R^{18}$ is independently $(CH_2)_p$, and
p is an integer of from 1 to 10.

6. A personal care composition, comprising water and a derivatized polysaccharide polymer, said derivatized polysaccharide polymer comprising a levan polyfructose polymer substrate bearing one or more cationic substituent groups wherein the levan polyfructose polymer substrate comprises fructosyl units that are linked by β,2-6 linkages and comprises formula (XI):

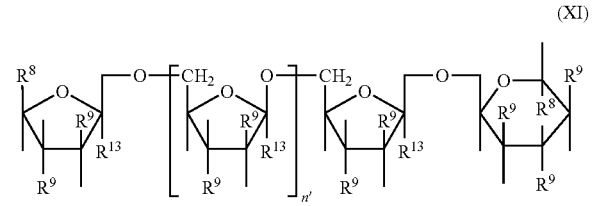

wherein:
n' is a number effective to provide a weight average molecular weight of from about $1\times10^4$ to about $1\times10^7$ Daltons, as measured by gel permeation chromatography
each $R^7$ is independently a cationic moiety
each $R^8$ is independently $CH_2OH$ or $CH_2R^7$,
each $R^9$ is independently OH or $R^7$,
each $R^{13}$ is independently $CH_2OH$, $CH_2R^7$, or $CH_2R^{14}$,
each $R^{14}$ is independently a fructosyl branch moiety according to structure (XII):

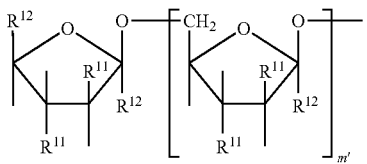

wherein each $R^{11}$ is independently OH or $R^7$, each $R^{12}$ is independently $CH_2OH$ or $CH_2R^7$, and each m' is independently 0, 1, 2, or 3, and provided that at least one $R^9$ is $R^7$, or at least one $R^{13}$ is $CH_2R^7$, or at least one $R^{13}$ is a fructosyl branch moiety according to formula (XII) and at least one $R^{11}$ is $R^7$ or at least one $R^{12}$ is $CH_2R^7$.

7. The personal care composition of claim 6, wherein the personal care composition is selected from cleansing compositions, conditioners, and hair styling products.

8. The personal care composition of claim 6, wherein the personal care composition is a hair care composition comprising, based on 100 parts by weight of the hair care composition, from about $1 \times 10^{-7}$ parts by weight to about 10 parts by weight of the derivatized polysaccharide polymer.

9. The personal care composition of claim 6, wherein the personal care composition further comprises one or more surfactant compounds selected from amphoteric surfactants, Zwitterionic surfactants, nonionic surfactants, anionic surfactants, cationic surfactants and mixtures thereof.

10. The personal care composition of claim 6, further comprising one or more additional ingredients selected from preservatives, thickeners, viscosity modifiers, electrolytes, pH adjusting agents, perfumes, dyes, organosilicon materials, anti-dandruff agents, vitamins, vitamin derivatives, and sequestering agents.

11. A skin care or hair care composition comprising the derivatized polysaccharide polymer of claim 1, skin care or hair car active ingredient, and water.

12. The composition of claim 11, further comprising an anionic surfactant.

13. The personal care composition of claim 6, wherein the composition further comprises an anionic surfactant, and
   (a) the composition comprises a discontinuous phase having higher relative amounts of derivatized fructan polymer and anionic surfactant than the overall composition, or
   (b) the composition does not comprises such a discontinuous phase, but upon dilution with water, the dilute composition forms such a discontinuous phase.

14. The personal care composition of claim 6, wherein the composition and the discontinuous phase each further comprise an active ingredient and the discontinuous phase aids in deposition of the active ingredient on the hair or skin.

15. The personal care composition of claim 6, wherein the active ingredient comprises a fragrance, a conditioning agent, or an anti-dandruff ingredient.

16. The polymer of claim 1 wherein the derivatized polysaccharide polymer is in the form of one or more nanoparticles.

17. The polymer of claim 16 wherein the nanoparticles exhibit, for greater than about 70% by weight of the nanoparticles, a hydrodynamic radius of about 76 nm.

18. The polymer of claim 1 wherein the epoxide is selected from the group consisting of 2,3-epoxypropyltrimethylammonium chloride, 2,3-epoxypropyldimethyl dodecylammoniumchloride, and mixtures thereof.

19. The personal care composition of claim 6 wherein the epoxide is selected from the group consisting of 2,3-epoxypropyltrimethylammonium chloride, 2,3-epoxypropyldimethyl dodecylammoniumchloride, and mixtures thereof.

20. The polymer of claim 1 wherein the polymer, in a 1% aqueous solution, is characterized by a viscosity of between 10 and 5,000 centipoise.

* * * * *